United States Patent [19]

Smith

[11] Patent Number: 5,606,966
[45] Date of Patent: Mar. 4, 1997

[54] TRACHEOSTOMY TUBE ASSEMBLY

[75] Inventor: Rory J. M. Smith, Skipton, Great Britain

[73] Assignee: Kapitex Healthcare Ltd., United Kingdom

[21] Appl. No.: 373,232

[22] PCT Filed: Jul. 8, 1993

[86] PCT No.: PCT/GB93/01429

§ 371 Date: Mar. 7, 1995

§ 102(e) Date: Mar. 7, 1995

[87] PCT Pub. No.: WO94/01158

PCT Pub. Date: Jan. 20, 1994

[30] Foreign Application Priority Data

Jul. 10, 1992 [GB] United Kingdom ............... 9214716

[51] Int. Cl.$^6$ .................................................. A61M 16/00
[52] U.S. Cl. ............................. 128/200.26; 128/207.17; 128/DIG. 26
[58] Field of Search ........................ 128/200.26, 207.14, 128/207.15, 207.17, DIG. 26

[56] References Cited

U.S. PATENT DOCUMENTS

| | | | |
|---|---|---|---|
| 3,263,684 | 8/1966 | Bolton | 128/207.16 |
| 4,304,228 | 12/1981 | Depel | 128/207.17 |
| 4,668,222 | 5/1987 | Poirier | 128/DIG. 26 |
| 4,669,763 | 6/1987 | Phillips | 285/346 |
| 4,971,054 | 11/1990 | Andersson et al. | 128/207.16 |
| 5,076,922 | 12/1991 | Deare | 210/282 |
| 5,146,913 | 9/1992 | Khorsandian et al. | 128/912 |
| 5,251,616 | 10/1993 | Desch | 128/912 |
| 5,259,378 | 11/1993 | Huchon et al. | 128/207.16 |

FOREIGN PATENT DOCUMENTS

| | | |
|---|---|---|
| 2647680 | 12/1990 | France . |
| 2159223 | 11/1985 | United Kingdom . |

*Primary Examiner*—Aaron J. Lewis
*Attorney, Agent, or Firm*—Merchant, Gould, Smith, Edell, Welter & Schmidt, P.A.

[57] ABSTRACT

A tracheostomy tube assembly comprises a tracheostomy tube (2), a fitting (4) to be mounted on the end of the tracheostomy tube (2), having a bore (6) in which teh end (8) of the tracheostomy tube (2) can be received, a sealing memeber (10) which can be located between the outer surface of the tracheostomy tube (2) adn the inner surface of the bore (6) in the fitting (4), and means (12) for urging the sealing member against the outer surface of teh tracheostomy tube to form a seal between the fitting (4) and the tracheostomy tube (2). The assembly allows a sealed connection to be made to the end of the tracheostomy tube (2), so that a filter (20, 32) or a valve (34) (for example to assist in speech) can be fitted over a tracheostoma.

10 Claims, 2 Drawing Sheets

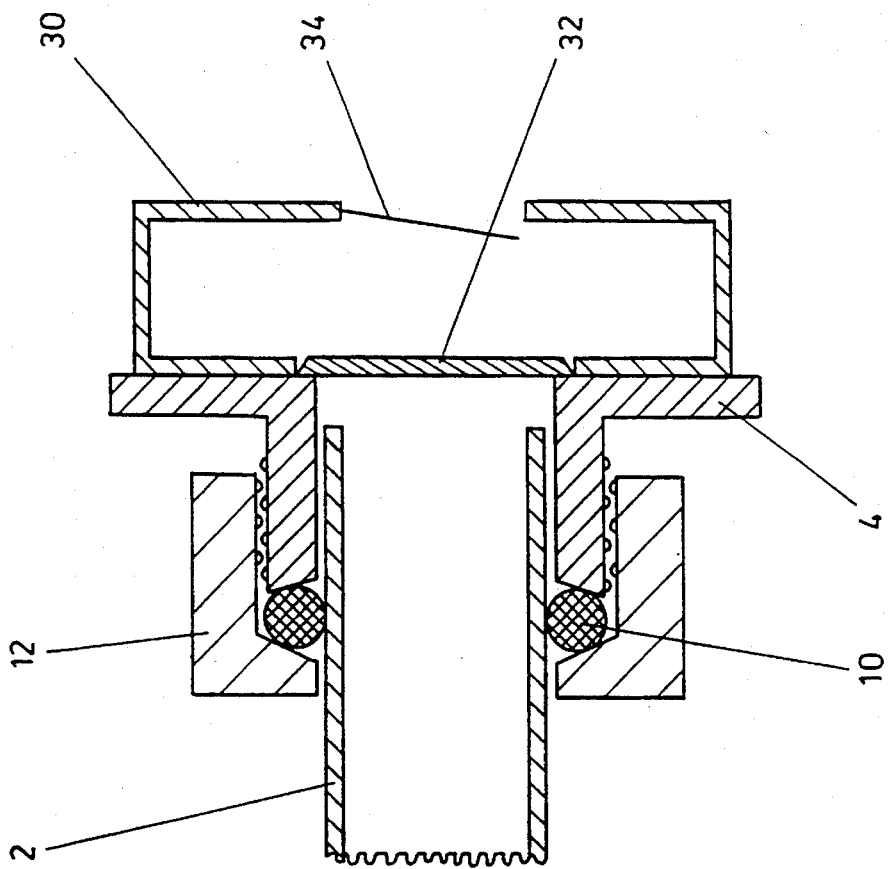
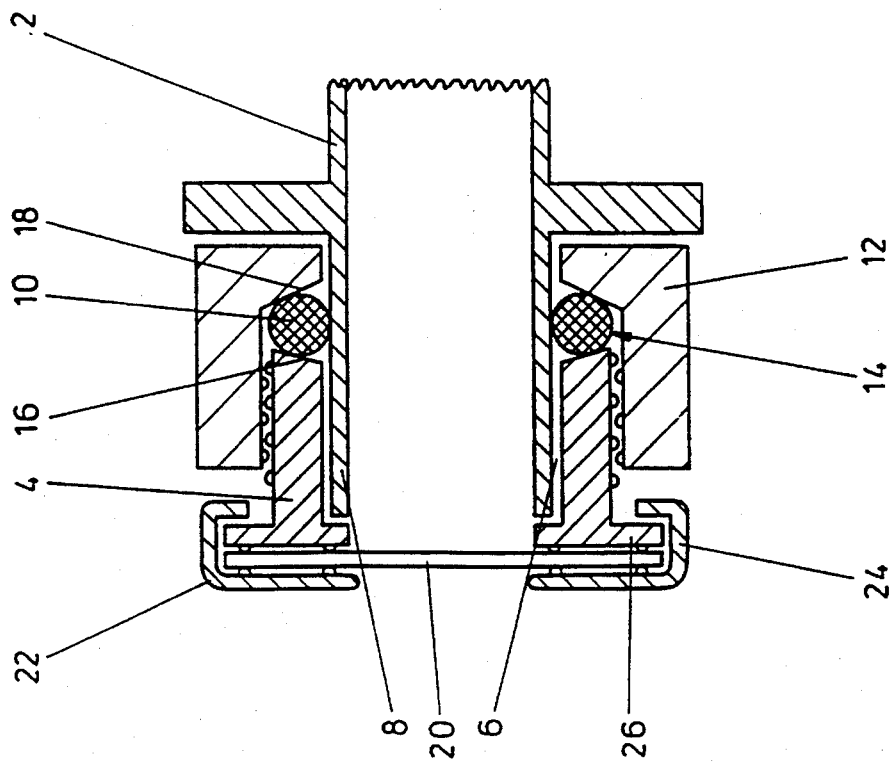
FIG. 1
FIG. 2

TRACHEOSTOMY TUBE ASSEMBLY

This invention relates to a tracheostomy tube assembly, which includes a tracheostomy tube and a fitting which can be mounted on the end of the tube.

A tracheostomy is a surgical procedure which creates an opening through the anterior surface of the neck into the trachea. The opening is referred to as a tracheostoma. It is performed to by-pass an upper airway obstruction, or to enable the provision of long term respiratory support via connection to a ventilator, or for some other medical reason. In order to enable the patient to speak it is necessary to provide a means of directing the flow of exhaled air through the larynx. This can conveniently be achieved by the incorporation of a valve. A tracheostomy tube can be provided to extend between the tracheostoma and the trachea.

A nasal simulation device serves to simulate some of the functions of the nose, and optionally can include a speaking valve to assist in diverting the flow of exhaled air to permit speech.

In a subject whose breathing functions normally, the nose and the mucous membrane lining of the nasal cavity perform important functions in conditioning incoming air. The convoluted passages and rich blood supply serve to increase both the temperature and humidity of the incoming air to minimise the differential in these parameters with those of the surface of the lungs. Normally some heat and moisture is also captured from exhaled air prior to its release to the atmosphere. The mucous lining of the nasal passages also serves to remove particles in the inhaled airstream, and the action of the cilia transports mucous and any particles away from the lungs.

The exchange of heat and moisture and filtration are clearly beneficial to the patient, and in their absence clinical consequences such as increased incidence of chest infections, elevated levels of secretion production and encrustation are observed.

When a patient has received a tracheostomy, in effect all inhaled air enters the lungs via the tracheostoma, and the nose is effectively not involved in the inhalation process. Exhaled air may pass through the tracheostoma or, if a voice prosthesis has been fitted, the stoma can be occluded so that the exhaled air is diverted through the voice prosthesis into the pharynx and the mouth, enabling the patient to speak. It is desirable that the flow of the exhaled air be controlled by means of a tracheostoma valve. In these situations, the valve can be arranged to remain open during breathing but, with a small additional increase in exhaled air pressure, can be closed to divert the air flow.

The present invention provides a tracheostomy tube assembly which enables a fitting to be mounted to the end of a tracheostomy tube, with a seal between the fitting and the tube.

Accordingly, in a first aspect, the invention provides a tracheostomy tube assembly, which comprises:

(a) a tracheostomy tube;

(b) a fitting to be mounted on the end of the tracheostomy tube, having a bore in which the end of the tracheostomy tube can be received;

(c) a sealing member which can be located between the outer surface of the tracheostomy tube and the inner surface of the bore in the fitting; and (d) means for urging the sealing member against the outer surface of the tracheostomy tube to form a seal between the fitting and the tracheostomy tube.

The assembly of the invention has the advantage that a fitting can be mounted on the end of a tracheostomy tube, with a seal between the fitting and the tube. By urging the sealing member against the outer surface of the tracheostomy tube, the fitting can be retained on the tube, so that it is resistant to becoming detached from the tube, for example as a result of movement of the user of the assembly, such as during eating or coughing. The fitting can be retained on the tube without any requirement for formations on the tube, which has the advantage that the assembly can be used with standard tracheostomy tubes. Indeed, assemblies can be supplied for fitting to tracheostomy tubes from other sources, or to tubes which have already been fitted to patients. Furthermore, and significantly, the fitting can be arranged to be capable of being removed from the end of the tube quickly, by releasing the urging means. This might be important when, for example, it is desired to connect the tracheostomy tube to other equipment such as to a ventilator.

The seal and between the tracheostomy tube and the fitting can be made without affecting the surface of the tube, by selection of an appropriate sealing member. This can be particularly advantageous when it becomes necessary to connect other equipment to the tracheostomy tube. An O-ring gasket of a resilient material has been found to be suitable for the sealing member.

The assembly of the invention allows a fitting to be mounted onto a tracheostomy tube without reduction of the bore size of the tube. Furthermore, the connection between the tube and the fitting can be achieved with a low profile fitting. This has the advantage of enabling the assembly to be used on tubes which only protrude a short distance from the tracheostoma.

The assembly can be used to locate a filter device on the end of a tracheostomy tube. The filter device can filter inhaled air to ensure that it does not carry matter that is filtered in a normal nasal cavity, such as fine dust particles, pollutants and micro organisms. The filter device can also include means for exchange of heat and moisture with inhaled air. A filter device which can be mounted on a tracheostomy tube using the assembly of the invention is disclosed in the application filed with the present application bearing the reference P21559WO which claims priority from UK patent application no 9214716.4, and which is entitled Filter device. Subject matter disclosed in the specification of that application is incorporated in this specification by this reference.

The filter device might be attached to the fitting by means of an adhesive. Preferably, the fitting has formations for engaging a filter device. The formations might include a slot which is open along at least one edge to allow a filter device to be inserted.

The assembly can include a housing, the housing and the fitting having complimentary formations by which they can engage one another. For example, the housing and the fitting might be provided with complimentary threads or mating portions of a bayonet fitting, or cooperating flanges which can engage one another by deformation of one or both of the flanges, for example in the manner of a container used for storage of food.

The housing may contain a valve, which might be relied on, for example, to divert exhaled air for generation of speech. The housing might include a filter device, or might be arranged to engage a filter device. For example, a filter device might be located between the housing and the fitting which the housing engages.

Preferably, at least one of the fitting and the urging means presents an inclined face to the sealing member, so that the sealing member can be deformed against the outer surface of the tracheostomy tube by being forced against the said inclined face. Especially, both the flitting and the urging means present inclined faces to the sealing member.

Preferably, the urging means comprises a sleeve member which can engage the fitting, with the sealing member located between them, and can be moved relative to the fitting to deform the sealing member into sealing contact with the outer surface of the tracheostomy tube. The sleeve member will generally be fitted around the tracheostomy tube. Generally, the surfaces of the fitting and the sleeve are shaped such that relative movement of the fitting and the sleeve towards each other causes the sealing member to be deformed and to be forced into sealing engagement with the external surface of the tracheostomy tube.

The fitting and the urging means will generally have complimentary formations by which they can engage one another. For example, they might have complimentary threads.

Conveniently, components of the assembly, especially the fitting and the sleeve member or other urging means, are formed from a rigid material, for example a polymeric material such as a nylon or a polycarbonate. They can be made by moulding.

The sealing member will generally be located in a cavity defined between the fitting and the sleeve member. Preferably, the cavity is defined by inclined end faces of the fitting and the sleeve member, such that relative movement of the member towards the fitting results in a reduction in the height of the cavity. This forces the sealing member into air tight engagement with both the tracheostomy tube and the fitting.

Embodiments of the present invention will now be described, by way of example, with reference to the accompanying drawings, in which:

FIG. 1 is a cross section through a tracheostomy tube assembly in which a filter has been attached to the end of the tube;

FIG. 2 illustrates the device of FIG. 1 with a speaking valve housing, in which a filter is attached to the housing;

Figure 4:
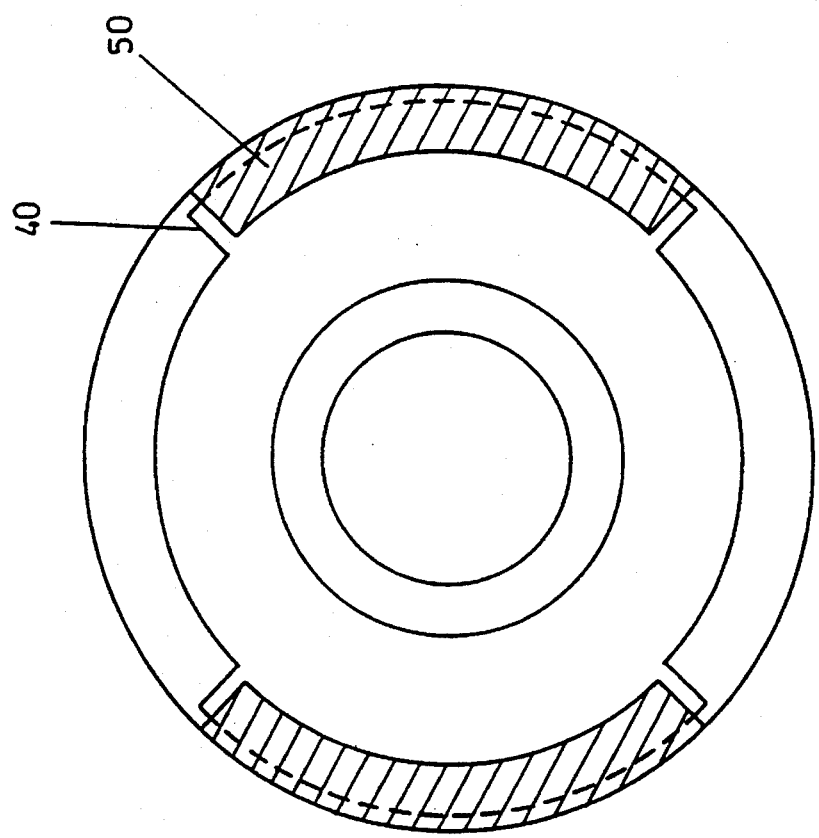
FIGS. 3 and 4 are transverse and rear elevational views, partially in section, of tracheostomy tube assembly to which a housing is attached by means of a twist lock mechanism.

Referring to the drawings, FIG. 1 shows a tracheostomy tube assembly which comprises a tracheostomy tube 2, and a fitting 4 having a bore 6 in which the end 8 of the tracheostomy tube can be received. The assembly includes a sealing member 10 in the form of a rubber O-ring. A sleeve member 12 is fitted onto the tracheostomy tube. The fitting 4 and the sleeve member 12 have complimentary threads and, when they engage one another, define a cavity 14 between them in which the sealing member 10 can be located.

The end faces 16, 18 of the fitting 4 and the sleeve member 12 are inclined so that the cavity 14 between them is longer at its base against the external surface of the tracheostomy tube than at the top. As the fitting and the sleeve member are drawn towards one another using the threads provided thereon, the sealing member 10 is forced by the inclined surfaces against the external surface of the tracheostomy tube, to form a seal between that surface and the fitting.

The deformation of the sealing member against the external surface of the tracheostomy tube ensures that the fitting is retained on the tube, so that it is not dislodged as a result of motion by the user. The connection between the fitting and the tracheostomy tube can however be released when required, quickly and simply, by disengaging at least partially the threads on the fitting and the sleeve member.

A filter 20 can be mounted on the tracheostomy tube 2 by fastening it to the externally facing surface of the fitting 4, for example by means of an adhesive, or by means of a holder 22 having a flange 24 which engages a cooperating flange 26 on the fitting.

FIG. 2 shows a tracheostomy tube assembly of the type shown in FIG. 1, in which a housing 30 is attached to the fitting 4 by means of an adhesive. A filter device 32 is retained in place between the housing and the fitting. The housing includes a valve 34 for controlling the flow of exhaled air, for example to permit speech.

Figure 3:
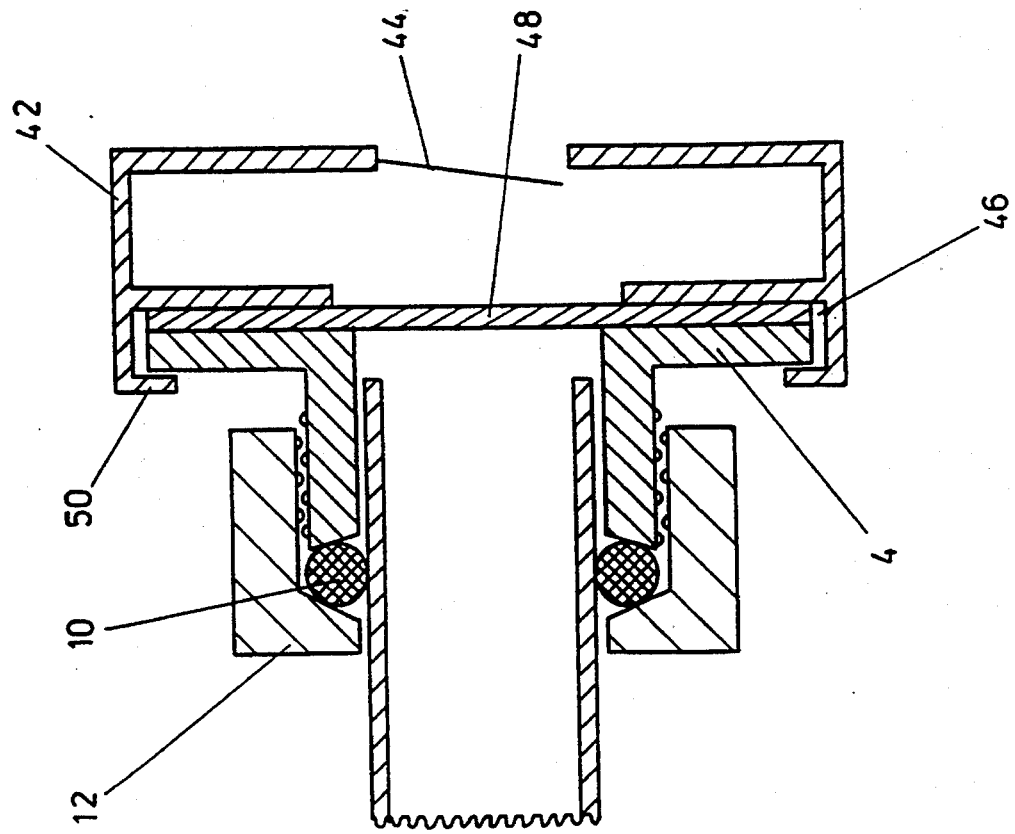

FIGS. 3 and 4 show a tracheostomy tube assembly in which the fitting 4 has a flange 40 with gaps formed in it. A housing 42 includes a valve 44 and a recess 46 for a filter device 48. The housing has a lip 50 formed around the face which is intended to face the fitting 4, the lip being broken around the circumference of the housing.

The breaks in the lip 50 on the housing and the gaps in the flange 40 on the fitting allow the lip to engage the flange and, by rotation of the housing relative to the fitting, to be retained on the housing.

I claim:

1. A tracheostomy tube assembly comprising:
   (a) a tracheostomy tube having an exposed end and an outer surface;
   (b) a fitting removably mounted on the exposed end of the tracheostomy tube, the fitting having a bore with an inner surface in which the end of the tracheostomy tube can be received;
   (c) a sealing member located between the outer surface of the tracheostomy tube and the inner surface of the bore in the fitting; and
   (d) means for urging the sealing member against the outer surface of the tracheostomy tube to form a seal between the fitting and the tracheostomy tube, the means for urging being mounted on the tracheostomy tube by way of the exposed end of the tracheostomy tube; and
   (e) the fitting and the urging means being removable from the tracheostomy tube by way of the exposed end of the tracheostomy tube while the tracheostomy tube is in a patient's tracheostoma.

2. An assembly as claimed in claim 1, in which at least one of the fitting and the urging means presents an inclined face to the sealing member, so that the sealing member can be deformed against the outer surface of the tracheostomy tube by being forced against the said inclined face.

3. An assembly as claimed in claim 2, in which both the fitting and the urging means present inclined faces to the sealing member.

4. An assembly as claimed in claim 1, in which the urging means comprises a sleeve member which can engage the fitting with the sealing member located between them, and can be moved relative to the fitting to deform the sealing member into sealing contact with the outer surface of the tracheostomy tube.

5. An assembly as claimed in claim 1, in which the fitting and the urging means have complimentary threads, by which they engage one another.

6. An assembly as claimed in claim 1, in which the fitting has formations for engaging a filter device.

7. An assembly as claimed in claim 6, in which the formations comprise a slot which is open along at least one edge to allow a filter device to be inserted.

8. An assembly as claimed in claim 1, which includes a housing, the housing and the fitting having complimentary formations by which they can engage one another.

9. An assembly as claimed in claim 8, in which the housing contains a valve.

10. An assembly as claimed in claim 8, in which the housing contains a filter.

* * * * *